United States Patent
Ibragimov

(10) Patent No.: US 8,317,499 B2
(45) Date of Patent: Nov. 27, 2012

(54) PULSATILE PERISTALTIC PUMP FOR USE IN A CARDIOPULMONARY BYPASS

(76) Inventor: Araz Ibragimov, Brooklyn, NY (US)

( * ) Notice: Subject to any disclaimer, the term of this patent is extended or adjusted under 35 U.S.C. 154(b) by 647 days.

(21) Appl. No.: 12/617,038

(22) Filed: Nov. 12, 2009

(65) Prior Publication Data

US 2010/0054975 A1 Mar. 4, 2010

Related U.S. Application Data

(60) Continuation-in-part of application No. 12/544,190, filed on Aug. 19, 2009, now Pat. No. 7,972,291, which is a division of application No. 11/283,323, filed on Nov. 18, 2005, now Pat. No. 7,578,662.

(51) Int. Cl.
- *F04B 43/12* (2006.01)
- *F04B 43/08* (2006.01)
- *F04B 45/06* (2006.01)

(52) U.S. Cl. .................................................. 417/477.3

(58) Field of Classification Search ............... 417/477.1, 417/477.3; 604/890.1–892.1, 131
See application file for complete search history.

(56) References Cited

U.S. PATENT DOCUMENTS

| | | | | |
|---|---|---|---|---|
| 3,790,313 A | * | 2/1974 | Magerle | 417/477.3 |
| 4,228,930 A | * | 10/1980 | Hogan | 222/212 |
| 4,492,531 A | | 1/1985 | Kenji | |
| 4,976,593 A | | 12/1990 | Miyamoto | |
| 5,643,172 A | | 7/1997 | Kung | |
| 5,709,539 A | * | 1/1998 | Hammer et al. | 417/477.3 |
| 5,820,579 A | | 10/1998 | Plotkin | |
| 5,890,626 A | * | 4/1999 | Wolski et al. | 222/129.1 |
| 5,916,191 A | | 6/1999 | Plunkett | |
| 6,170,707 B1 | * | 1/2001 | Wolski et al. | 222/129.1 |
| 6,406,267 B1 | | 6/2002 | Mondiere | |
| 6,506,035 B1 | * | 1/2003 | Beck et al. | 417/477.3 |
| 6,547,753 B1 | | 4/2003 | Plunkett | |
| 6,810,713 B2 | * | 11/2004 | Hahn et al. | 73/23.35 |
| 7,866,960 B2 | * | 1/2011 | Parng | 417/477.5 |
| 2002/0071776 A1 | * | 6/2002 | Bandis et al. | 417/477.6 |
| 2003/0026719 A1 | * | 2/2003 | Hahn et al. | 417/476 |
| 2003/0143754 A1 | * | 7/2003 | Lum et al. | 436/180 |
| 2007/0134113 A1 | * | 6/2007 | Parng | 417/477.3 |

* cited by examiner

*Primary Examiner* — Devon Kramer
*Assistant Examiner* — Ryan Gatzemeyer
(74) *Attorney, Agent, or Firm* — Boris Leschinsky

(57) ABSTRACT

The peristaltic pump of the invention incorporates at least one pumping roller and one occluding roller. The occluding roller is located diametrically across the pumping roller and is designed to provide occlusion only and not progressive squeezing of the pump tubing while rotating in the same direction as the pumping roller. Such occlusion prevents back-flow through the tubing. More than two rollers spaced evenly along the periphery of the rotor allow for various useful combinations of pumping and occluding rollers. Two occluding and one pumping roller combination creates a pulsatile flow close to that of a human heart—with systole being about twice shorter than diastole.

4 Claims, 3 Drawing Sheets

PULSATILE PERISTALTIC PUMP FOR USE IN A CARDIOPULMONARY BYPASS

CROSS-REFERENCE DATA

This application is a continuation-in-part of a U.S. patent application Ser. No. 12/544,190 filed Aug. 19, 2009 entitled "A single-needle dialysis system utilizing a peristaltic pump with pumping and occluding rollers", which in turn is a divisional application of a U.S. patent application Ser. No. 11/283,323 filed Nov. 18, 2005 entitled "Peristaltic pump having pumping and occluding rollers and alternating pumping systems utilizing thereof", now U.S. Pat. No. 7,578,662, both documents incorporated herein in their entirety by reference.

BACKGROUND OF THE INVENTION

The natural human heart provides the body with a pulsatile flow of blood corresponding to the filling and emptying (beating) of the various chambers of the heart. The instantaneous blood flow rate varies in a complex cyclical manner from near zero to some maximum rate, with the overall blood flow rate being a time weighted average.

The cardiopulmonary bypass circuits of heart-lung machines used in open-heart surgery typically utilize centrifugal or positive displacement (i.e. roller type) pumps to provide the motive power for circulation of the blood. These pumps provide an essentially constant flow rate of blood through the circuit at all times, the instantaneous rate and the average rate being nearly identical.

The basic roller pump consists of two rollers, 180 degrees apart, that rotate in a circle through a half circular raceway. A length of flexible tubing between ¼ and ⅝ inch inner diameter is placed between the rollers and the raceway. The rollers rotating in a circular movement compress the tubing against the raceway, squeezing the blood ahead of the rollers. The rollers are set to almost completely occlude the tubing, and operate essentially as a positive displacement pump, each passage of a roller through the raceway pumping the entire volume of the fluid contained in the tubing segment between the rollers. As a positive displacement pump, high positive pressures can be generated at the pump outlet and high suction (negative) pressures can be generated at the pump inlet. Roller pumps are typically driven by a constant speed motor which draws blood at a substantially constant rate.

Medical studies have suggested that pulsatile flow, being more physiologically correct than constant flow, may have a beneficial impact on the efficacy of the extracorporeal perfusion. This can result in improved patient outcomes following cardiac bypass surgery. Pulsatile flow is important for cerebral oxygenation and autoregulation, and for other tissue perfusion and capillary blood flow. Cerebral hypoperfusion is a known problem in cardiopulmonary bypass. Neonates require a pulsatile flow. Native pulsatile flow stimulates the endothelial cells that line normal blood vessels, causing them to elongate and secret local factors (endothelium-derived relaxing factor [nitric oxide] and prostaglandin $I_2$ [$PGI_2$, or prostacyclin]) into the vessel wall (intramural release) and into the blood stream (intraluminal release). These factors maintain vascular tone (vessel relaxation), inhibit clot formation on the vessel inner surface (platelet adhesion and aggregation), inhibit monocyte adherence and chemotaxis, and inhibit smooth muscle cell migration and proliferation. There are other effects. U.S. Pat. No. 5,643,172 associates failure to provide a pulsatile flow with high incidence of renal dysfunction during ECMO followed by recovery after the return to pulsatile flow.

Various ways have been proposed to mimic in a heart-lung machine the natural pulsatile flow of the heart, but none of them have so far been satisfactory. The simplest way of providing a pulsed flow is to cyclically clamp and unclamp the inlet or outlet line of the heart-lung machine's arterial pump. Clamping the pump inlet is not desirable since it can create very high suction pressures in the inlet which can damage the red blood cells, or in some cases even cause cavitation which can potentially release gas bubbles into the blood stream. Further, during the low flow or rest periods, the pump rotors spin on a stagnant volume of fluid, which may result in mechanical trauma to the blood cells. Clamping the pump outlet is not desirable in a centrifugal pump due to this mechanical trauma. Clamping the pump outlet is not desirable in a positive displacement pump since the rapid buildup of pressure in the lines can rupture the connections or tubing, potentially resulting in a catastrophic event.

A more acceptable way of creating pulsatile flow is to vary the speed of the pump in a cyclical manner. This is easily accomplished electronically by the pump controller. However, the inertia of the spinning elements of the pump tends to render the resulting waveform more sinusoidal than the natural heartbeat waveform and forces the wave period to be longer than the natural period. In addition, the components of the bypass circuit downstream of the pump, such as the oxygenator and arterial filter, also damp the pulses due to their volumetric holdup.

A pump in the prior art which, unlike the roller pump and the centrifugal pump, is provided with regulating devices to control the available pumping volume so the output is controlled as a function of inlet pressure, was invented by A. Sausse, described in U.S. Pat. No. 3,784,323, incorporated herein by reference. This pump, originally designed for use in hemodialysis, was commercialized for a period of time by Rhone-Poulenc, S.A., as the RP.01 through RP.06 series of pumps.

The Sausse (Rhone-Poulenc) pump stretches a distensible silicon tubing of an ovoid or elliptical cross section and shape memory compliance longitudinally around pin rollers mounted 120 degrees apart on a rotating wheel, the tubing being held in place below the wheel by connectors retained in a notched fixed base. This tubing, herein called a "header" tubing, is not compressed against a raceway (as for a roller pump), but is held in tension across the rollers, restricting the lumen of the header tubing across the rollers. This segments the header tubing into portions defined by leading and trailing adjacent rollers. The rotation of the wheel moves fluid captured between adjacent rollers in the direction of the rotation. The material and thickness of the wall of the header tubing are selected so the tubing between the rollers will expand or collapse as a function of pump inlet pressure (available venous return). Collapse of the tube will restrict the flow rate of the liquid as a function of the pump inlet pressure. If the venous supply decreases and inlet pressure drops, flow rate will lessen even though the pump speed is unchanged, and the inlet line will remain filled. Consequently, no dangerously low negative pressures can occur, unlike what is possible with roller and centrifugal pumps. When outflow obstruction occurs, the liquid blocked from flowing forward can back flow, so the pump feeds nothing forward to over pressurize and burst the return line. Instead, the back flow accumulates in the stretched header tubing, which distends or expands to accommodate the additional volume. When the obstruction is released, blood flows downstream propelled by the increased stroke volume of the distended header tubing. The header tubing stretched over the rollers therefore functions as a built-in capacitance reservoir, eliminating the need for the reservoirs that are required for roller and centrifugal pumps.

The flow rate of the Sausse type pump may be considered as substitute cardiac output and pump suction volume as diverted venous return. The compliance of the header tube allows its volume to increase under the action of the suction pressure. The volume is evacuated in the form of a bolus, and its evacuation causes the tube to regain a flat shape capable for being refilled. This compliance provides a level of security that is similar to that of a reservoir.

Lastly, a reciprocating type pump such as a diaphragm or bladder pump can be employed to create pulses in the flow. These pumps tend to be more mechanically complex than the roller or centrifugal types and do not lend themselves to either easy cleaning, sanitation, and sterilization for reuse, or low cost manufacture for one-time disposable use. Increased blood trauma is experienced in these pumps due to the multiple check valves in the flow path and stagnant areas due to less than perfect chamber filling and ejection. Lastly, as mentioned above, downstream components still damp the pulses and thus reduce the beneficial effects of the reciprocating pump.

The detailed rationale for pulsatile flow is described in a book co-authored by Linda B. Mongero and Kames R. Beck entitled "On bypass: advanced perfusion techniques"—published by Humana Press in 2008. Pages 102-114 deal with the issue of pulsatile flow during bypass and are incorporated herein in their entirety by reference.

Despite many attempts to deliver pulsatile flow, no blood pump adapted for this purpose is routinely used today. The need still exists for a simple peristaltic pump capable of delivering pulsatile flow during an open heart surgery.

SUMMARY OF THE INVENTION

Accordingly, it is an object of the present invention to overcome various drawbacks of the prior art by providing a novel roller pump capable of producing pulsatile flow while being operated at a constant speed of rotation.

It is another object of the invention to provide a roller pump capable of providing pulsatility of flow mimicking that of a human heart, e.g. at a systole-to-diastole ratio of about 1 to 2.

It is a further object of the invention to provide a roller pump configuration adapted for easy replacement on a traditional heart-lung machine system.

The roller pump of the invention is based on the general principle of incorporating at least one pumping roller and one occluding roller into the peristaltic mechanism of the pump. The pumping roller is made similar to the rollers of known peristaltic pumps. The occluding roller located for example diametrically across the pumping roller is designed to provide occlusion only and not progressive squeezing of the pump tubing while rotating in the same direction as the pumping roller. Such occlusion prevents back-flow through the tubing. More than two rollers spaced evenly along the periphery of the rotor allow for various useful combinations of pumping and occluding rollers. Two occluding and one pumping roller for example create a pulsatile flow close to that of a human heart—with the systole being about twice shorter than diastole.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS OF THE INVENTION

A detailed description of the present invention follows with reference to accompanying drawings in which like elements are indicated by like reference letters and numerals.

Figure 1:
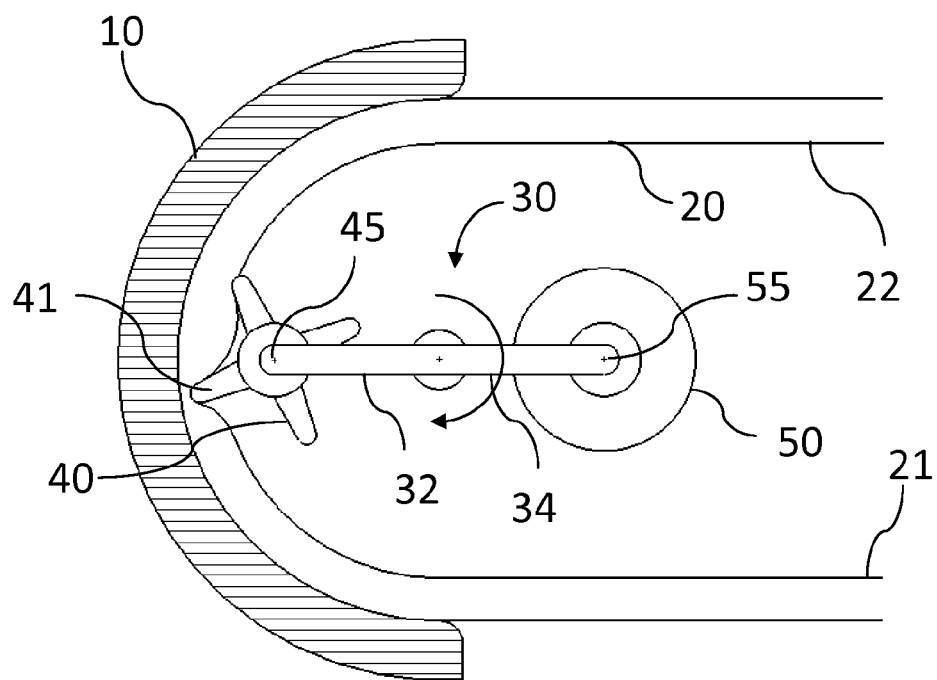
FIG. 1 is a general top view of the first embodiment of the pump of the invention with the rotor having an occluding roller and a pumping roller, the occluding roller is shown interacting with the tubing of the pump.

The roller pump of the first embodiment of the invention is shown in FIG. 1 and comprises a housing having a central axis and a half-circular raceway 10; a rotor 30 having a center 35 and containing one occluding roller 40 and one pumping roller 50. Occluding roller 40 has an occluding roller axis 45 and is adapted for free or actively-driven rotation at the end of a rotor arm 32. The pumping roller 50 having the same diameter as the roller 40 is rotatably supported about a pumping roller axis 55 at the end of the rotor arm 34. The pumping roller axis 55 and the occluding roller axis 45 are 180° apart. A flexible tubing 20 is placed along the raceway 10 between the housing and the rotor 30 and contains an inlet 21 and an outlet 22 as defined by the clockwise rotation of the rotor 30 shown by an arrow in FIG. 1.

Figure 2:
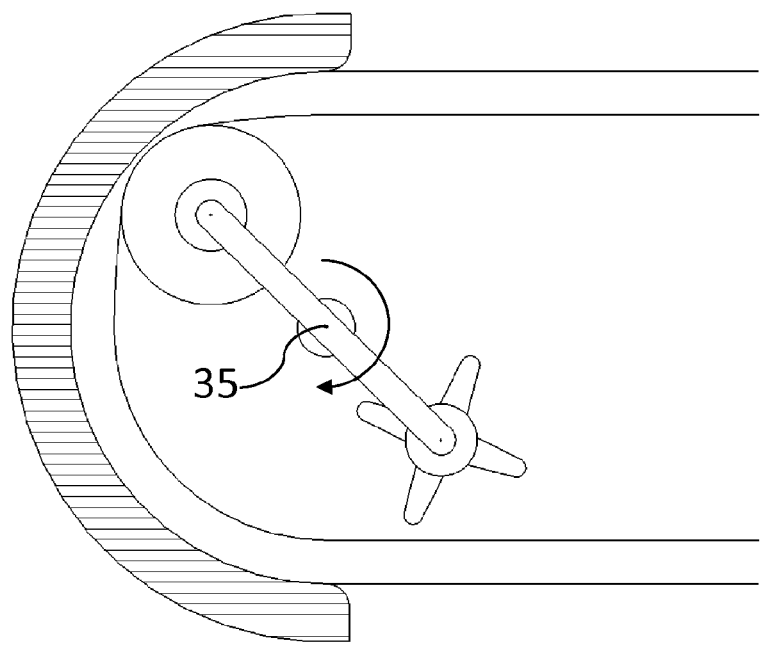
FIG. 2 is a general top view of the pump of FIG. 1, the pumping roller is shown interacting with the tubing of the pump.
Figure 4:
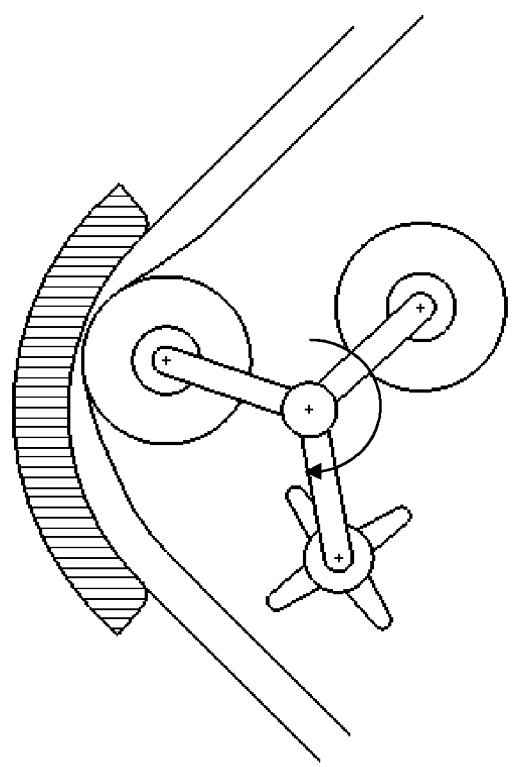
FIG. 4 is a general top view of the pump of FIG. 3, one pumping roller is shown interacting with the tubing of the pump.
Figure 6:
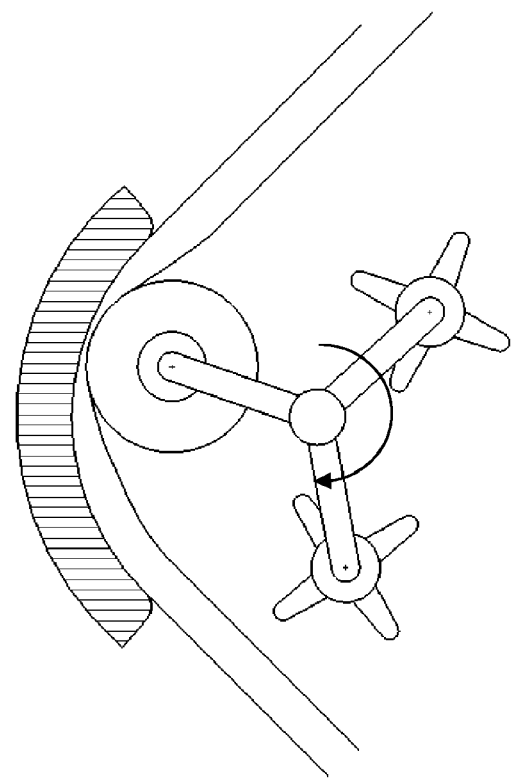
FIG. 6 is a general top view of the pump of FIG. 5, a pumping roller is shown interacting with the tubing of the pump.

The round pumping roller 50 is made using common design principles of peristaltic pumps. It has smooth circular outer surface designed to occlude the pump tubing 20 and to progressively squeeze the fluid out of it along the raceway in the direction of rotation of the rotor 30. FIGS. 2, 4, and 6 show the interaction of the pumping roller 50 with the tubing 20 as the pumping roller 50 is moved forward by the rotor 30 of the pump. The diameter of the round pumping roller is the same as the outer diameter of the occluding roller.

The occluding roller 40 is equipped with a plurality of radial protrusions 41 (four protrusions shown in FIG. 1) equally spaced apart. The quantity and the shape of protrusions 41 are determined by the actual design of the pump and the tubing used therein. Importantly, the design of the occluding roller 40 allows for occluding the tubing 20 during its operation and preventing any back flow therethrough from the outlet to the inlet. The protrusions 41 are also spaced apart sufficiently to allow the tubing to achieve at least a partial recovery of a non-compressed shape in its section located between the adjacent protrusions of the occluding roller 40. The outer ends of the radial protrusions define the outer diameter of the occluding roller.

Active and passive designs of occluding roller are contemplated within the scope of this invention. An active design (not shown) involves causing each of the occluding rollers to rotate with a predetermined speed related to the speed of rotation of the main rotor 30. Gear drives may be used for this purpose—internal gears within the rotor 30 as well as external gear links to the corresponding gear elements associated with the raceway 10. Using actively driven occluding roller allows for a better control of the engagement of the roller with the tubing 20 at the beginning of the raceway 10 and disengagement of the roller 40 from the tubing 20 at the end of the raceway 10 so as to minimize hemolysis of the pump.

The radial raceway 10 of the pump is defined by a segment having an angle equal to 360 degrees divided by a total number of occluding and pumping rollers, in this case 2. This embodiment therefore has a raceway located along a 180 degree arch.

Figure 3:
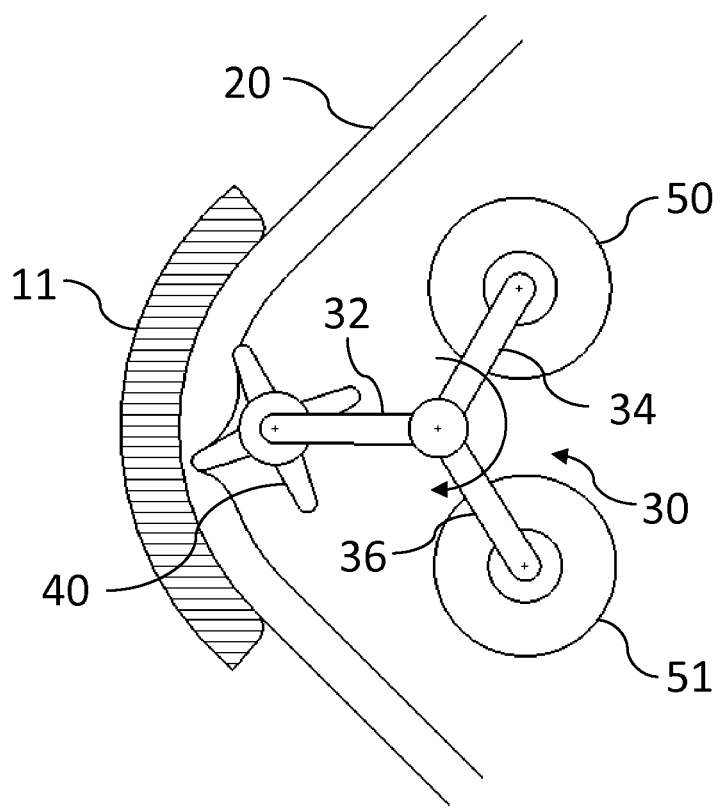
FIG. 3 is a general top view of the second embodiment of the pump of the invention with the rotor having an occluding roller and two pumping rollers, the occluding roller is shown interacting with the tubing of the pump.
Figure 5:
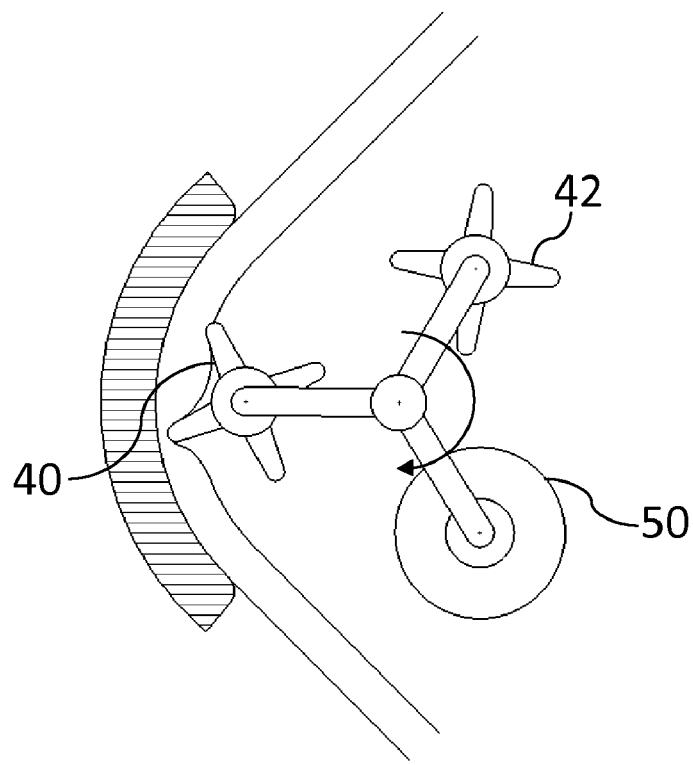
FIG. 5 is a general top view of the third embodiment of the pump of the invention with the rotor having two occluding rollers and one pumping roller, the occluding roller is shown interacting with the tubing of the pump; and finally

Interaction of the occluding roller 40 and the tubing 20 of the pump is shown in FIGS. 1, 3, and 5.

In operation, the pump tubing is connected to a source of fluid, for example to a venous blood reservoir in a case of its use in a heart-lung machine. The outlet is connected to other components of the system culminating in a return arterial cannula. The rotor 30 is turned by an electrical motor. Due to the length of the raceway 10 being ½ of the circumference of the rotor 30, one of the two rollers 40 or 50 is in contact with the tubing 20. When the pumping roller 50 is moved over the tubing 20, it is squeezed by the roller causing flow in a direction towards the pump outlet. When the occluding roller 40 is moved over the tubing 20, its protrusions 41 compress the tubing 20 but cause no progressive squeezing of the fluid therefrom. As a result, the tubing 20 is compressed at certain points along its length to prevent any back flow but also no forward flow is occurring.

This configuration is designed to cause forward flow through the tubing during ½ of each revolution of the rotor while the remaining ½ of each revolution of the rotor cause tubing occlusion without forward or backward flow. As a result, this design allows for an even split between forward flow and no-flow.

FIGS. 3 through 6 show two more embodiments of the invention in which the rotor 30 supports three rollers thereon. FIG. 3 and FIG. 4 illustrate a second embodiment of the invention where the there is a single occluding roller 40 rotatably supported at the end of the rotor arm 32. Two pumping rollers 50 and 51 are rotatably supported by the rotor arms 34 and 36 respectably. The rotor arms are spaced apart evenly at 120° from each other. Importantly, the length of the raceway 11 is selected to also cover ⅓ of the circumference of the rotor 30. Having three rollers define the segment angle of the raceway as 360° divided by 3 equal to 120°. This configuration allows for a split in the delivery of the flow over a single revolution of the rotor of ⅔ flow and ⅓ no-flow.

FIG. 5 and FIG. 6 show a configuration of the third embodiment of the invention which is similar to that of the second except for having one pumping roller 50 and two occluding rollers 40 and 42. Operating of this pump provides for a split in the flow delivery over each rotor revolution of ⅓ flow and ⅔ no-flow. This configuration is particularly advantageous for use in a heart-lung machine as it mimics closely a ratio of systole to diastole of 1 to 2.

One particularly advantageous configuration of this embodiment is a roller pump assembly sized to fit on standard heart-lung machines—it can replace traditional roller pumps and provide for pulsatile flow cardiopulmonary bypass without incurring much expense to the hospital.

More than three rollers can also be used with the pump of the invention. Importantly, all rollers have to be spaced apart along the periphery of the rotor evenly and the raceway has to cover only an arch having an angle equal to the angle between the adjacent rollers. Multiple rollers provide for an even more precise opportunity to adjust the split between flow and no-flow using the pump of the invention. For example 5 rollers (2 occluding and 3 pumping) allow for a 60/40 split of flow/no-flow. The angle of the arch of the raceway is determined by dividing 360 by the total number of rollers: 180° for 2 rollers, 120° for 3 rollers, 90° for 4 rollers, etc. Remaining portion of the pump housing supports the tubing in a non-occlusive way to direct it towards other elements of the bypass system.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A pulsatile flow peristaltic pump comprising:
   a first occluding roller having a first occluding roller axis and a plurality of equally spaced apart radial protrusions defining an outer diameter thereof,
   a first round pumping roller having a first pumping roller axis and an outer diameter being substantially the same as the outer diameter of the first occluding roller,
   a rotor having a center and a periphery, said rotor rotatably supporting said first occluding roller at the first occluding roller axis, said rotor further rotatably supporting said first pumping roller as the first pumping roller axis, said occluding roller axis and said pumping roller axis being evenly spaced along the periphery of the rotor at the same distance from the center thereof,
   a housing with a central axis and a radial raceway along a segment with an angle being about equal to 360 degrees divided by a total number of pumping and occluding rollers of said pump, said housing rotatably supporting said rotor such that the center of the rotor is at the central axis of the housing, and
   an elastic tubing placed along the raceway between the rotor and the housing, said tubing having an inlet and an outlet,
   whereby upon rotation of said rotor said pump producing a forward flow from the inlet to the outlet when said pumping roller is engaged with said tubing to progressively squeeze thereof along said raceway, said pump preventing backflow from said outlet to said inlet without producing forward flow when said occluding roller is engaged with said tubing to progressively occlude thereof by its radial protrusions along said raceway, said tubing recovering at least partially to an uncompressed shape between adjacent protrusions of said occluding roller.

2. The peristaltic pump as in claim 1 further including a second round pumping roller of the same diameter as the first pumping roller, said second pumping roller being rotatably supported by said rotor at a second pumping roller axis, all rollers being equally spaced apart along the periphery of the rotor at the same distance from the center thereof, said radial raceway being along a segment having an angle of about 120 degrees, whereby forward flow is caused during two-thirds of each revolution of the rotor and tubing occlusion is caused during remaining one-third of each revolution of the rotor.

3. The peristaltic pump as in claim 1 further including a second occluding pumping roller of the same diameter as the first occluding roller, said second occluding roller being rotatably supported by said rotor at a second occluding roller axis, all rollers being equally spaced apart along the periphery of the rotor at the same distance from the center thereof, said radial raceway being along a segment having an angle of about 120 degrees, whereby forward flow is caused during one-third of each revolution of the rotor and tubing occlusion is caused during remaining two-thirds of each revolution of the rotor.

4. The peristaltic pump as in claim 1 having at least one additional pumping or occluding rotor of the same outer diameter as said first occluding rotor or said first pumping rotor, all rollers being equally spaced apart along the periphery of the rotor at the same distance from the center thereof, whereby forward flow is caused during a part of each revolution of the rotor defined as a ratio of a number of pumping rollers divided by a number of all rollers, while tubing occlusion is caused during a part of each rotor revolution defined as a ratio of a number of occluding rollers divided by a number of all rollers.

* * * * *